(12) United States Patent
Raupach et al.

(10) Patent No.: US 8,218,721 B2
(45) Date of Patent: Jul. 10, 2012

(54) X-RAY BEAM MODIFYING DIAPHRAGM AND DIAPHRAGM DEVICE

(75) Inventors: Rainer Raupach, Heroldsbach (DE); Bernhard Schmidt, Nuremberg (DE)

(73) Assignee: Siemens Aktiengesellschaft, Munich (DE)

(*) Notice: Subject to any disclaimer, the term of this patent is extended or adjusted under 35 U.S.C. 154(b) by 348 days.

(21) Appl. No.: 12/570,197

(22) Filed: Sep. 30, 2009

(65) Prior Publication Data
US 2010/0091937 A1 Apr. 15, 2010

(30) Foreign Application Priority Data
Sep. 30, 2008 (DE) .......... 10 2008 049 708

(51) Int. Cl.
*G21K 1/04* (2006.01)
*H05G 1/60* (2006.01)
(52) U.S. Cl. .......... 378/16; 378/150
(58) Field of Classification Search .......... 378/150–153, 378/145, 158, 147–148, 4, 19, 15–17
See application file for complete search history.

(56) References Cited

U.S. PATENT DOCUMENTS

| | | | |
|---|---|---|---|
| 4,464,778 A | 8/1984 | Goldmann | |
| 5,396,533 A | 3/1995 | Holzermer | |
| 6,480,570 B1 * | 11/2002 | Ikeda | 378/98.7 |
| 6,501,828 B1 * | 12/2002 | Popescu | 378/150 |
| 7,336,768 B2 * | 2/2008 | Ogawa | 378/156 |
| 2001/0019599 A1 | 9/2001 | Guendel | |
| 2005/0243422 A1 | 11/2005 | Distler et al. | |
| 2006/0050841 A1 | 3/2006 | Distler et al. | |
| 2006/0262897 A1 | 11/2006 | Raupach | |

FOREIGN PATENT DOCUMENTS
DE 196 25 864 C2 10/1999

* cited by examiner

*Primary Examiner* — Irakli Kiknadze
(74) *Attorney, Agent, or Firm* — Schiff Hardin LLP

(57) ABSTRACT

A diaphragm and diaphragm device for the specific manipulation of x-ray radiation that emanates from an x-ray focus of a CT apparatus and serves for scanning an examination subject, wherein the x-ray focus and the diaphragm arranged relatively near to the focus can be rotated together around a system axis (z-axis), and the diaphragm has movable diaphragm elements that dynamically adjust a diaphragm aperture (and therefore the spatial divergence of the x-rays passing through the diaphragm aperture). The diaphragm elements have a transmission factor for x-ray radiation that is different than zero. With such a diaphragm or diaphragm device the acquisition of the projection data necessary for the reconstruction of an artifact-free image of a region of interest (ROI) is possible with lower radiation exposure of the examination subject.

21 Claims, 5 Drawing Sheets

X-RAY BEAM MODIFYING DIAPHRAGM AND DIAPHRAGM DEVICE

BACKGROUND OF THE INVENTION

1. Field of the Invention

The present invention concerns a diaphragm for a specific manipulation (modification) of x-ray radiation that emanates from an x-ray focus, such as a CT apparatus, and that serves for scanning an examination subject, of the type wherein the x-ray focus and the diaphragm arranged relatively closer to the focus can be rotated together around a system axis (z-axis) and the diaphragm has movable diaphragm elements by means of which a diaphragm aperture—and therefore the spatial divergence of the x-rays passing through the diaphragm aperture—is dynamically adjustable. Furthermore, the invention concerns a diaphragm device and a CT apparatus, with such a diaphragm.

2. Description of the Prior Art

A CT apparatus for scanning an examination subject has, as is known at least one x-ray source with an x-ray focus from which a pyramid- or fan-shaped x-ray beam is directed through the examination subject (for example a patient) onto a detector system made up of multiple detector elements. The fan or pyramid shape of the x-ray beam is thereby typically matched to the detector system that is used so that the detector system is always completely exposed by the x-ray beam. The measurement area ("field of view", FOV) of the x-ray tube detector system is therefore also established. Depending on the design of the CT apparatus, the x-ray source and the detector system are mounted, for example, on a gantry or a C-arm that can rotate around a system axis (z-axis). Furthermore, a positioning device for the examination subject is provided that can be moved or displaced along the system axis (z-axis).

During the CT acquisition, each of the detector elements of the detector system that is struck by the x-ray radiation produces a signal that represents a measure of the total transparency of the examination subject for the radiation emanating from the radiation source on its path to the detector system, i.e., it represents the radiation attenuation. The set of output signals of the detector elements of the detector system that is acquired for a specific position of the radiation source is designated as a projection. The position of the x-ray focus from which the x-ray beam emanates and penetrates the examination subject is continuously varied as a result of the rotation of the gantry/the C-arm. The current position of the x-ray focus or of the detector system can be specified in polar coordinates (r, z, φ) for a given system axis (z-axis). During operation, the r-coordinates of the radiation source and of the associated detector system are typically constant. A scan of the examination subject thus includes a number of projections that have been respectively acquired at different positions of the gantry of the C-arm and/or at the various positions of the positioning device. A differentiation is made between sequential scanning methods and spiral scan methods. Based on the (projection) measurement data generated in a scan, 2D or 3D image data of the examination subject can be reconstructed by means of known methods.

Conventionally, the examination subject is scanned utilizing the FOV of the x-ray tube detector system. Particularly in examinations in which only a small volume section (ROI, "region of interest") of the examination subject is of interest, this leads to an exposure of an examination subject volume that is markedly larger in comparison to the ROI. The examination subject (for example a patient) is subjected unnecessarily to high radiation exposure since the examination subject is exposed in the entire measurement field of the x-ray tube detector system (FOV), but the actual ROI is significantly smaller by many times than the FOV.

To avoid an unnecessary radiation exposure given a scan of an examination subject with a CT apparatus, from DE 102 42 920 A1 a diaphragm device is known with which the beam can be adjusted in a very precise manner on the measurement field of the detector. The diaphragm device has a diaphragm with two radiator-side absorber elements that adjust the x-ray beam emanating from the x-ray focus. The diaphragm is fashioned so that the two absorber elements can be positioned with a high positioning precision before the beginning of an examination.

A CT apparatus with two diaphragms arranged in series is known from DE 196 25 864 C2, which diaphragms serve to gate a pyramidal x-ray beam. Only the diaphragm situated farther away from the focus is adjustable.

A primary beam diaphragm is known from DE 42 29 321 A1 in which two diaphragm pairs can each be adjusted in opposite directions in two parallel planes so that a rectangular gating of the x-ray beam is possible.

Moreover, from DE 31 36806 A1 an x-ray examination apparatus is disclosed which has an x-ray tube with different adjustable focal spots and an adjustable diaphragm. Upon switching the focal spot, the diaphragm can be displaced synchronously in the same direction and by approximately the same amount by which the focal spot is displaced.

Furthermore, from DE 10 2005 018 811 B4 a diaphragm device is known in which at least two diaphragms are provided for beam shaping during the scanning of an examination subject, wherein for at least one segment of the scan a beam adjusted with the first diaphragm can be at least partially dynamically masked out by means of the second diaphragm, and wherein the adjustment of the beam by the first diaphragm can be implemented with a high positional accuracy and the dynamic masking by the second diaphragm can be implemented with a high positioning speed.

Some of the diaphragms or diaphragm systems cited above allow a specific scanning of a predetermined ROI in an examination subject. With the known diaphragms or the diaphragm systems, a dynamic limitation of the spatial divergence of the x-ray beam used for scanning the examination subject ensues at the ROI. X-rays that are directed to regions outside of the ROI are thereby masked out. A marked reduction of the radiation dose acting on the examination subject (on the order of 50%) can be achieved. However, for an artifact-free image reconstruction of the projection data that are acquired using such known diaphragms or systems, the problem exists that projection data outside of the ROI are also required, at least for folding within the scope of filtered back-projection. This problem is presently solved by implementing a scan with a full measurement field (FOV) of the x-ray tube detector system before the implementation of the dynamic scan that is limited to an ROI. From the scan with the full measurement field (FOV), the necessary projection data for the image reconstruction with the needed supplementary data are available for all later dynamic scans. However, this assumes that nothing changes at the position of the ROI during the entire dynamic scan. If the examination subject (for example a patient) moves during the examination, the data supplementation from the pre-scan is incorrect and leads to image artifacts.

SUMMARY OF THE INVENTION

An object of the present invention is to provide a diaphragm and a diaphragm device for a CT apparatus with which the acquisition of the projection data necessary for reconstruction of an artifact-free image of a region of interest (ROI) is achieved with the least possible radiation exposure of the examination subject, wherein the region of interest (ROI) is smaller than the maximum possible measurement region (FOV) of the x-ray tube detector system of the CT apparatus and is generally not centrally located on the rotation axis.

According to the invention, a diaphragm is provided for the specific manipulation of x-ray radiation that emanates from an x-ray focus of a CT apparatus and serves for the scanning of an examination subject, wherein the x-ray focus and the diaphragm arranged relatively near to the focus can be rotated together around a system axis (z-axis), and the diaphragm has movable diaphragm elements by which a diaphragm aperture (and therefore the spatial divergence of the x-rays passing through the diaphragm aperture) can be dynamically adjusted, and the diaphragm elements have a transmission factor for x-ray radiation that is different than zero.

As used herein, "transmission factor", means the quotient of the x-ray intensity in the radiation direction before a diaphragm element and the radiation intensity in the radiation direction after the diaphragm element. The transmission factor is thus a measure of the radiation intensity "let through" in the radiation direction. A transmission factor different than zero therefore means that x-rays striking the diaphragm elements penetrate the diaphragm elements, thus are usable to scan the examination subject and generate corresponding projection data. The transmission factor is advantageously measured so that the transmitted x-rays generate evaluable measurement signals at the detector system for an image reconstruction. Alternatively, the degree of the attenuation of the x-rays emanating from the x-ray focus that is achieved by the diaphragm elements can also be specified as an attenuation factor.

This indicates by what factor the radiation intensity is attenuated upon passing through a diaphragm element. In order to generate evaluable measurement signals, the x-ray radiation attenuation factor of the diaphragm elements lies at a value <20,000.

As used herein "spatial divergence", means the spatial aperture angle of an x-ray beam emanating from the x-ray focus.

The invention proceeds from the insight that although projection data outside of the ROI are also necessary for the reconstruction of artifact-free image data of a region of interest (ROI) of the examination subject that is smaller than the measurement region (FOV) of the x-ray tube detector system; such projection data outside of the ROI essentially enter into (contribute to) the reconstruction only with their low-frequency components. This is due to the fact that the basic convolution kernel of the inverse Radon transformation in frequency space is provided by a linear slope. Consequently, a markedly higher noise can be tolerated in the projection data that acquire the examination subject outside of the ROI. The intensity of the x-rays that serve to scan the region surrounding the ROI can therefore be reduced by a significant factor so that these x-rays practically do not contribute to the total dose striking the examination subject but nevertheless generate evaluable measurement data for the reconstruction at the detector system.

Instead of masking of x-rays as is done by known beam shaping diaphragms, in the diaphragm according to the invention a specific, there is a dynamic manipulation of an x-ray beam that emanates from the x-ray focus and passes through the diaphragm unattenuated to scan the examination subject, and the x-rays striking the diaphragm element outside of the diaphragm aperture can likewise be used to scan (irradiate) the examination subject with a correspondingly attenuated radiation intensity that is, however, still high enough to generate evaluable measurement signals at the detector system. The scanning of the examination subject thus ensues with an x-ray beam that has an unattenuated x-ray intensity and adjacent x-rays that have a reduced x-ray intensity.

In a preferred embodiment, at least two oppositely situated diaphragm elements are provided that are dynamically adjustable depending on the current position of the x-ray focus. Since the position of the x-ray focus in a scan is typically directed in a circular or spiral path around the examination subject, the diaphragm aperture is thus adjustable depending on the position of the x-ray focus on this circular or spiral path. The adjustment of the diaphragm elements can ensue, for example, by a mechanical, a magnetic, an electrical or an electromechanical actuator. The activation of the actuator ensues via a control device using information available to the control device regarding the current position of the x-ray focus. Naturally, the diaphragm elements can also be activated or adjusted depending on other or additional parameters.

Depending on the intended environment in which the diaphragm is used, as well as dependent its activation, the diaphragm aperture can exhibit any of a variety of peripheral shapes. The peripheral shape of the diaphragm aperture typically corresponds to a rectangular shape so that an unattenuated pyramidal or fan-shaped x-ray beam can be adjusted by the diaphragm aperture.

The diaphragm is advantageously executed such that the x-ray radiation passing through the diaphragm aperture corresponds to a fan-shaped x-ray beam that can be defined by a fan angle $\phi$ and a cone angle $\delta$, the fan angle $\phi$ being dynamically adjusted by means of the diaphragm elements.

In a further preferred embodiment, the diaphragm is executed such that the x-ray radiation passing through the diaphragm aperture corresponds to a fan-shaped x-ray beam that can be defined by a fan angle $\phi$ and a cone angle $\delta$, wherein the cone angle $\delta$ can be dynamically adjusted by the diaphragm elements.

Naturally, the diaphragm can also be executed such that a simultaneous adjustment of the fan angle $\phi$ and the cone angle $\delta$ of the diaphragm elements is possible depending on the position of the x-ray focus.

The diaphragm elements can particularly advantageously be adjusted such that only a predetermined region of interest (ROI) of the examination subject can be scanned with x-rays passing through the diaphragm aperture. It is thus possible to scan the examination subject in the ROI with the unattenuated x-rays passing through the diaphragm aperture and to acquire projection data from the region surrounding the ROI with the x-rays striking the diaphragm elements. In contrast to the known methods, projection data that can be used for the folding therefore also exist outside of the ROI at the same time as the scan of the ROI. The reconstructed image naturally has an increased noise outside of the ROI, but inside the ROI it can be reconstructed with full image quality.

Multiple possibilities enter into the tangible embodiment of the diaphragm elements. The diaphragm elements can each exhibit identical transmission properties for the x-ray radiation. The transmission properties of the diaphragm elements can naturally also differ, but diaphragm elements arranged opposite one another in the diaphragm advantageously have the same transmission properties. It is furthermore advantageous for the diaphragm elements to have homogeneous transmission properties for the x-ray radiation. Homogeneity hereby means the uniformity of the transmission properties over the entire expanse of a diaphragm element.

In one embodiment, the diaphragm elements are executed such that they attenuate the x-ray radiation striking them with a constant attenuation factor in the radiation direction. In the beam path after the diaphragm, an x-ray beam cross section with two intensity regions thereby results. A first region has a high, unattenuated x-ray intensity and proceeds from the x-rays that pass through the diaphragm aperture. A second region has an attenuated x-ray intensity and proceeds from the x-rays that strike the diaphragm elements.

The diaphragm elements are advantageously designed such that the x-rays striking the diaphragm elements in the radiation direction all pass through an identical diaphragm element thickness. However, at the detector system this embodiment leads to an abrupt change of the measured intensity profile at the boundary of the intensity regions designated above, i.e. for those x-rays that strike the diaphragm in the region of the peripheral edge of the diaphragm aperture. Due to this fast change of the intensity profile at the detector system, a calibration in this region is problematical. This situation can be alleviated by the corresponding projection data being removed from the measurement data and replaced with interpolated data, with typical interpolation methods (linear, polynomial etc.) being used. Given replacement, a larger projection data range on both sides of the intensity discontinuity is advantageously removed in order to account for tolerances in the adjustment of the positioning of the diaphragm elements and the focus position.

The attenuation of the x-ray intensity that is produced by the diaphragm elements is advantageously a factor of 2-100, in particular 10-20. Thus, given an attenuation of the x-ray intensity by a factor of 20 by the diaphragm elements given a use of the diaphragm according to the invention, approximately 45% of the dose is spared that would, in a conventional scan of the examination subject, strike in the entire FOV. Furthermore, given the use of the diaphragm according to the invention the first scan with full measurement field (FOV) is omitted in comparison to the previously known, dynamically adjustable diaphragms, such that an additional reduction of the dose acting on the examination subject thereby results.

The diaphragm elements preferably are formed of Ti or Cu or an alloy of Ti and Cu. Furthermore, the diaphragm elements preferably exhibit a diaphragm element thickness of 1 to 20 mm.

In one embodiment, the diaphragm elements respectively possess a constant diaphragm element thickness over the entire expanse of a diaphragm element.

In an alternative embodiment, the diaphragm element thickness of the diaphragm elements respectively increases or decreases from the side of the diaphragm elements facing towards the diaphragm aperture in the direction of the outside of the diaphragm. In one embodiment, the transmission factor for x-ray radiation of the diaphragm elements decreases starting from the side of the diaphragm elements facing towards the diaphragm aperture in the direction of the outside of the diaphragm. Due to the different diaphragm element thicknesses, a corresponding distribution of the attenuation factors that can be realized by means of the diaphragm elements results along their extent.

The above object is also achieved in accordance with the invention by a diaphragm device embodying a diaphragm of the type described above. Such a diaphragm device is for targeted manipulation of x-ray radiation that emanates from an x-ray focus of a CT apparatus and serves for the scanning of an examination subject, and the x-ray focus and the diaphragm device arranged relatively close to the focus can be rotated together around a system axis (z-axis). The diaphragm device has a first diaphragm with which an x-ray beam emanating from the x-ray focus can be adjusted and a second diaphragm with which the x-ray beam can be dynamically affected as described above.

The x-ray beam emanating from the x-ray focus, in particular its spatial divergence, is adjusted with the first diaphragm, which typically is arranged closer to the x-ray focus than the second diaphragm. The second diaphragm affects this x-ray beam in the manner explained in the preceding. The diaphragm device is advantageously characterized in that the first diaphragm can be adjusted with a high positioning precision and the second diaphragm can be adjusted with a high positioning speed. In one embodiment, the first diaphragm and the second diaphragm are adjusted in parallel with one another.

The diaphragm according to the invention, the diaphragm device according to the invention and a CT apparatus with such a diaphragm or diaphragm device enable a marked reduction of the dose affecting the examination subject if it is imperative to reconstruct artifact-free image data only for an ROI that is smaller than the FOV of the CT apparatus that is used or, respectively, its x-ray tube detector system. Through the position-dependent dynamic adjustment capability of the diaphragm according to the invention, during a dynamic scan the ROI can be scanned with unattenuated x-ray intensity and at the same time the region surrounding the ROI can be scanned with a markedly attenuated x-ray intensity. Due to the attenuated x-ray intensity of the x-rays used for the scanning of the region outside of the ROI, the noise of the corresponding projection data is increased. Insofar as projection data that can be used for folding within the scope of the reconstruction exist for regions outside of the ROI, at least the ROI can be reconstructed without artifacts.

DESCRIPTION OF THE PREFERRED EMBODIMENTS

Figure 1:
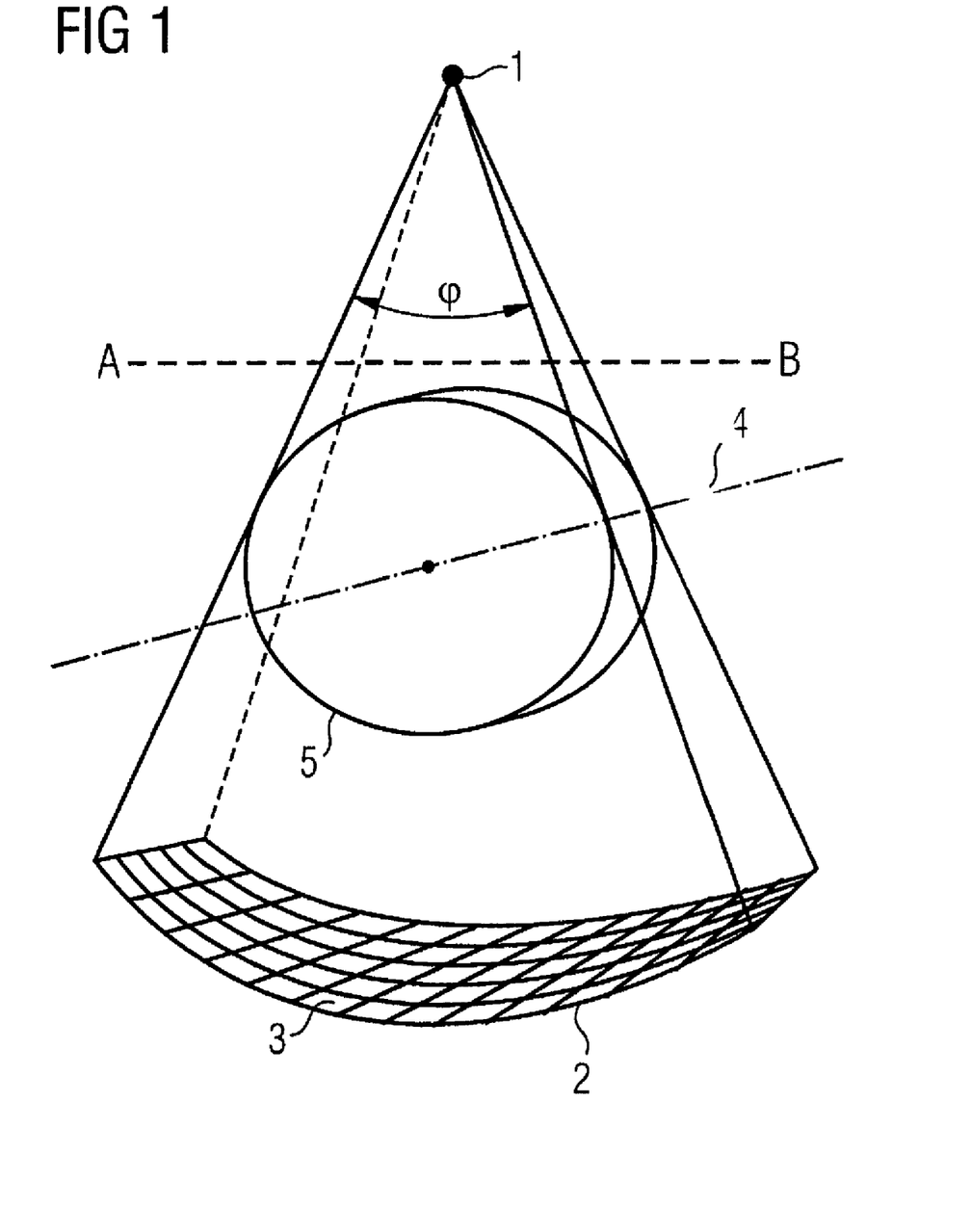
FIG. 1 is an illustration of the angle ratios of an x-ray beam emanating from an x-ray focus and scanning an FOV.

FIG. 1 shows an illustration of the angle ratios of an x-ray beam emanating from an x-ray focus 1 and that scans an FOV 5 and ultimately strikes a detector system 2 that is composed of multiple detector elements 3 organized in rows and columns. The x-ray beam emanating from the x-ray focus 1 is typically adjusted at the detector system 2 in a CT apparatus such that the x-ray beam completely exposes the detector system 2. The present beam has a fan-shaped geometry that can be described with a fan angle φ and a cone angle δ. Known beam shaping diaphragms are used for beam shaping in the prior art. The system axis (z-axis) 4 is likewise indicated in FIG. 1. For conventional scanning of an examination subject in the FOV, the x-ray focus detector system 1, 2 is rotated around the system axis 4 or, respectively, possibly shifted along the system axis 4.

Figure 2:
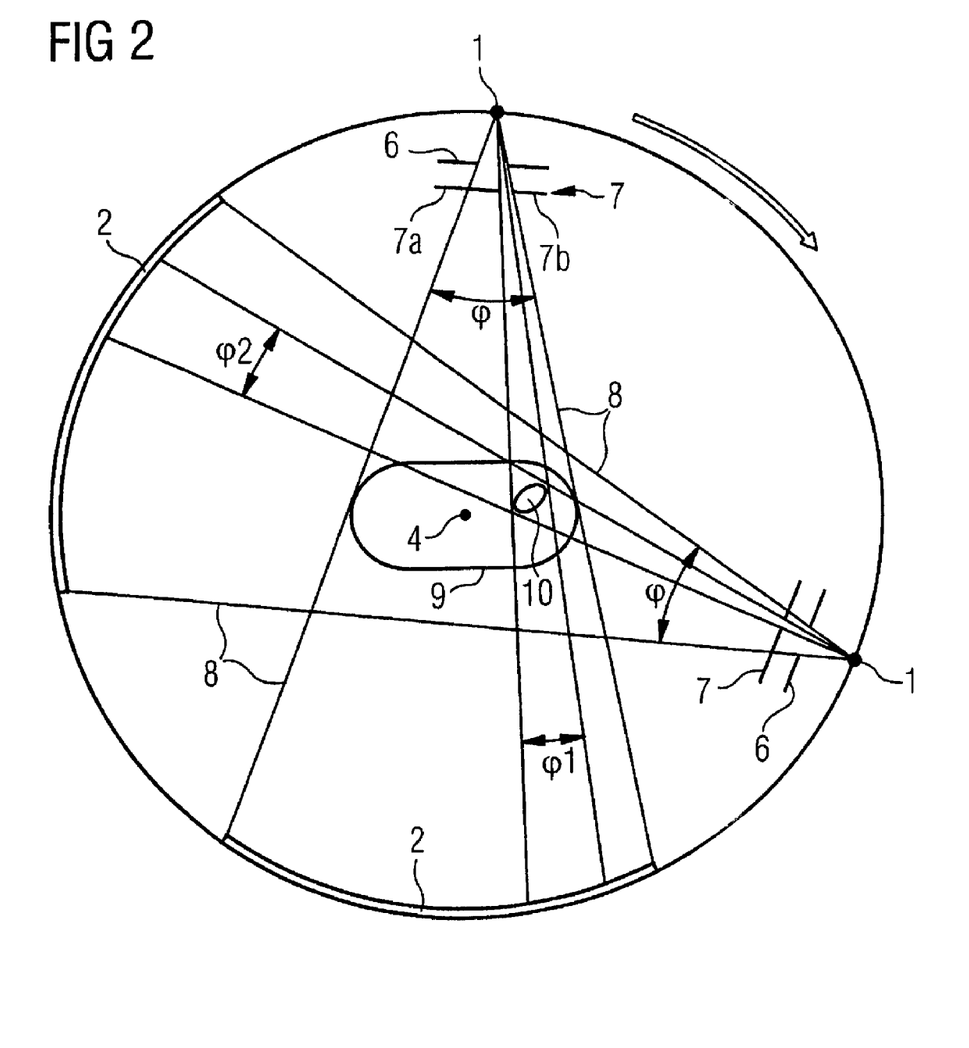
FIG. 2 is a schematic representation of the scanning of an ROI by means of an x-ray beam affected by a diaphragm device according to the invention.

FIG. 2 schematically shows the scanning of an examination subject 9 arranged within the FOV by means of an x-ray beam affected by a diaphragm device 6, 7 according to the invention. An x-ray focus detector system 1, 2 can be rotated clockwise around the system axis (z-axis) 4 situated perpendicular to the image plane for two selected x-ray focus positions The x-rays emanating fro the x-ray focus 1 initially strike a diaphragm device 6, 7 comprising two diaphragms. This diaphragm device 6, 7 has a conventional beam shaping diaphragm 6 with diaphragm elements impermeable to x-rays, which diaphragm elements limit the x-rays emanating unattenuated from the x-ray focus 1 to a beam so that the detector system 2 can be completely exposed. An x-ray beam is thus generated in the φ-direction by the first diaphragm 6, this x-ray beam being bounded by the edge rays 8 and matched to the dimension of the detector system in the φ-direction. In other words, via the first diaphragm 6 the fundamental fan angle φ is adjusted so that the detector system 2 is completely exposed with this.

It should be noted that the statements related to the fan angle φ in the preceding and in the following apply analogously to the cone angle δ.

A second diaphragm 7 is provided in the beam direction of the first diaphragm 6. This diaphragm 7 possesses two movable diaphragm elements 7a, 7b by means of which the diaphragm aperture in the φ-direction (and therefore the spatial divergence of the x-rays passing through the diaphragm aperture in the φ-direction) can be dynamically adjusted. According to the invention, each of the diaphragm elements 7a, 7b for x-ray radiation has a transmission factor that is different than zero. Given the rotation of the x-ray focus detector system 1, 2 around the system axis 4, the beam shaping diaphragm 6 always remains set so that the x-rays passing through it can completely expose the detector system. The divergence of the x-rays emanating from the x-ray focus is therefore limited to a constant fan angle φ. This x-ray beam strikes the diaphragm 7 that can be dynamically adjusted depending on the respective position of the x-ray focus 1. The x-rays passing through the diaphragm aperture of the diaphragm 7 are consequently unattenuated. In this exemplary embodiment the diaphragm elements 7a and 7b are adjusted depending on the position of the x-ray focus such that they are always directed towards a predeterminable region of interest (ROI) 10. The corresponding divergence angles φ1, φ2 of the x-rays passing unattenuated through the diaphragm 7 thus change within the fan angle φ depending on the position of the x-ray focus 1.

Figure 3:
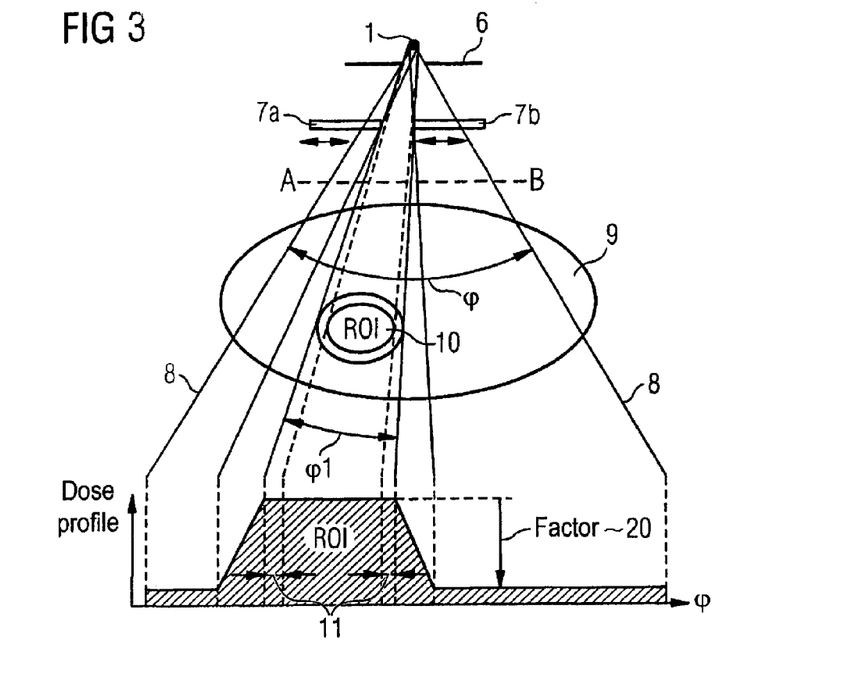
FIG. 3 is a schematic representation of the dose profile in the beam path between a diaphragm device according to the invention and the examination subject.

FIG. 3 shows a schematic representation of the dose profile in the beam path between the diaphragm device 6, 7 and the examination subject 9 along a beam cross section A-B (see FIG. 1 in this regard). As has already been explained with regard to FIG. 2, the upper image segment shows the x-ray radiation emanating from the x-ray focus 1 that is affected by the diaphragm device 6, 7 before this strikes the examination subject 9. Due to the (in reality finite) expanse of the x-ray focus 1, a somewhat greater divergence angle for φ (first diaphragm 6) and for φ1 (second diaphragm 7) results than given a point-shaped x-ray focus.

The dose profile of the x-ray radiation along the cross section line A-B is shown in the lower partial Figure of FIG. 3. The dose is thereby plotted along the ordinate, the fan angle φ along the abscissa. It is clearly recognizable that the ROI is scanned with the unattenuated x-ray dose while, in contrast to this, the regions of the examination subject surrounding the ROI are scanned by x-rays that are attenuated by a factor of 20 in terms of their intensity by diaphragm elements 7a, 7b of the diaphragm 7. The dose correspondingly falls or rises in the transition region, i.e. for the x-rays that pass through the diaphragm 7 in the peripheral region of the diaphragm aperture.

Figure 4:
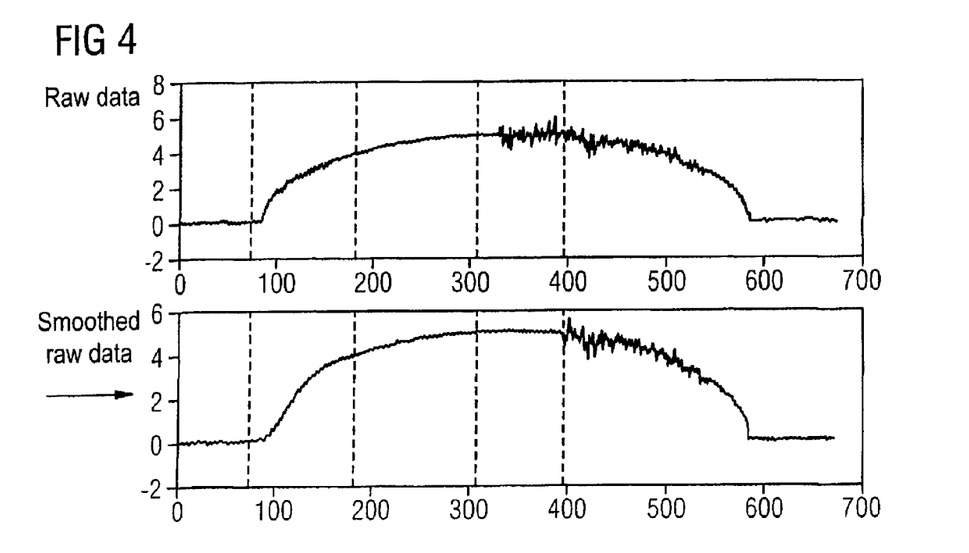
FIG. 4 is a representation of the raw detector data depending on the dose profile, and depiction of the data smoothed in the transition region between unattenuated x-rays and attenuated x-rays.

Raw data acquired by the detector system 2 are shown in FIG. 4, which raw data exemplarily result when the examination subject 9 is scanned with x-rays that correspond to the dose profile shown in FIG. 3. In the two graphs of FIG. 4, the signal value is plotted along the ordinate and the detector units along the fan angle φ are plotted along the abscissa, respectively. It can clearly be seen in the upper graph of FIG. 4 that the signal noise for projection data that represent the ROI are markedly lower than for projection data that represent regions outside of the ROI. Due to the fast change of the intensity profile at the detector 2, the corresponding measurement values in the transition region are removed from the measurement data and replaced with interpolated data. Given replacement, a larger projection data region to both sides of the intensity discontinuities is advantageously removed in order to account for tolerances in the adjustment of the positioning of the diaphragm elements and the focus position, for example. This tolerance range is identified with the reference character 11 in FIG. 3.

Typical interpolation methods are used.

The lower graph from FIG. 4 shows the projection data smoothed with the interpolated data. These projection data subsequently form the basis of the folding within the scope of the reconstruction of image data.

FIGS. 5-8 and 11 show different diaphragm element profiles for diaphragm elements 7a, 7b according to the invention. The arrows indicate that the diaphragm elements 7a, 7b can be dynamically positioned in the indicated φ-direction in the beam path emanating from the x-ray focus 1, wherein a corresponding change of the diaphragm aperture situated in the center of the respective two diaphragm elements 7a, 7b results. The shown diaphragms 7 are respectively irradiated from above with x-rays emanating from the x-ray focus 1. Those x-rays that pass through the diaphragm aperture are not attenuated by the diaphragm 7; the x-rays striking the diaphragm elements 7a and 7b are attenuated by an attenuation factor in terms of their intensity.

Figure 5:
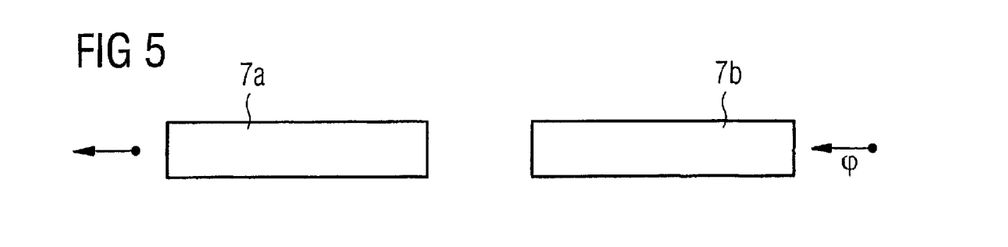
FIGS. 5-8 show examples of schematic diaphragm element cross sections.

In FIG. 5, the diaphragm elements 7a, 7b have a constant diaphragm element thickness over the expanse of the diaphragm element. However, the x-rays striking these diaphragm elements 7a and 7b travel through the diaphragm elements on paths of different lengths depending on the angle of incidence, which produces different attenuations of the incident x-rays depending on the beam path.

Figure 6:
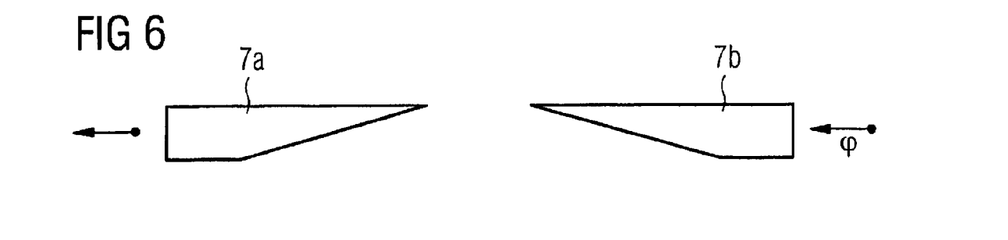
Figure 7:
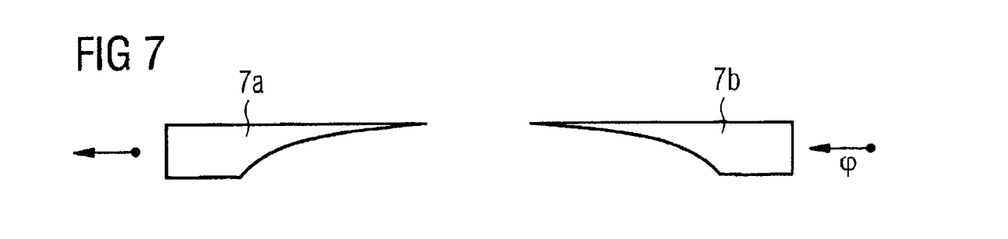

In FIGS. 6 and 7, the diaphragm element thickness increases from the side of the diaphragm elements 7a, 7b facing toward the diaphragm aperture in the direction of the outside of the diaphragm. A softer transition from unattenuated x-rays to attenuated x-rays therefore results. The final thickness of the diaphragm elements 7a, 7b is advantageously selected such that these correspond to an attenuation factor of 10-40, in particular 20. In addition to the possibilities shown FIGS. 6 and 7, there are arbitrary further possibilities for the concrete curve of the increase of the diaphragm element thickness.

Figure 8:
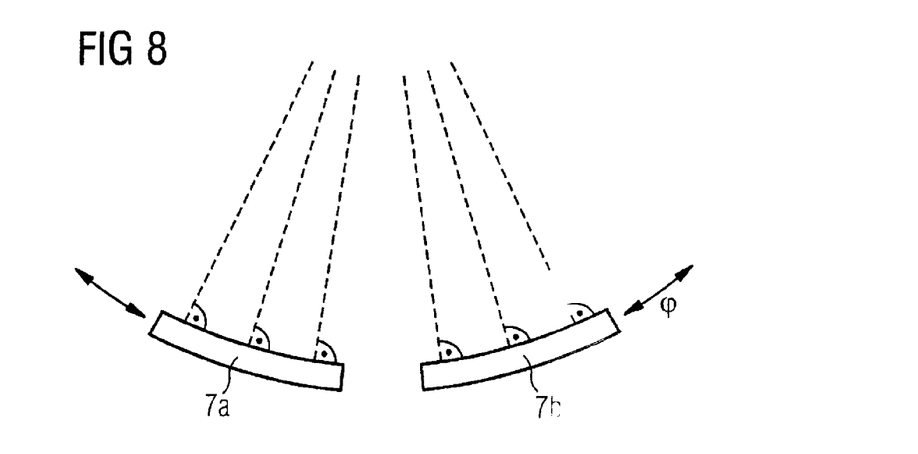

Finally, in FIG. 8 a diaphragm element shape is shown that possesses a constant diaphragm element thickness that, however, is shaped so that x-rays striking it always strike at right angles. With this it is ensured that these x-rays are all attenuated with the identical factor, wherein a homogeneous material distribution in the diaphragm elements 7a, 7b is assumed.

Figure 11:
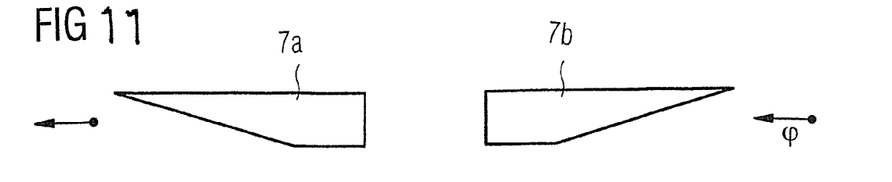
FIG. 11 shows a further example of a schematic diaphragm element cross section.

In FIG. 11, the diaphragm element thickness decreases from the side of the diaphragm elements 7a, 7b facing toward the diaphragm aperture in the direction of the outside of the diaphragm.

Figure 9:
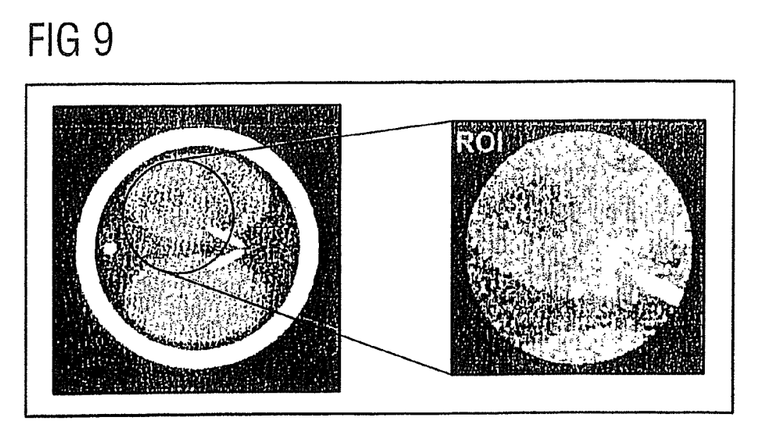
FIGS. 9-10 show reconstructed image data from projection data that have been acquired from an examination subject, wherein the examination subject in FIG. 9 was scanned conventionally with unattenuated x-rays and in FIG. 10 was scanned by means of x-rays affected by a diaphragm device according to the invention.
Figure 10:
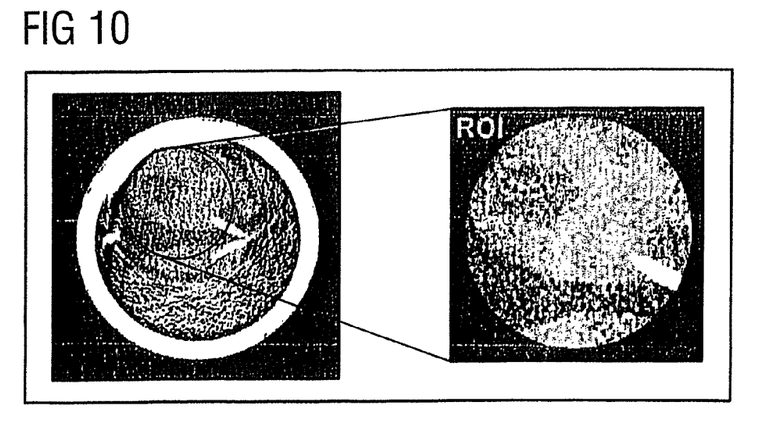

FIGS. 9 and 10 show reconstructed image data (2D images) from projection data that were acquired from an examination subject including ROI, wherein the two images in FIG. 9 are based on projection data that were conventionally generated via scanning of the examination subject 9 with unattenuated x-rays in the entire FOV while the two images in FIG. 10 are based on projection data that were generated via scanning of the examination subject 9 with x-rays which have been affected by a diaphragm device according to the invention. The respective right images of FIGS. 9, 10 show section enlargements of the respective left images for the ROI. With the application of conventional scanning methods (FIG. 9), the entire FOV (thus also the ROI) is reconstructed without artifacts. However, as described in the preceding, the examination subject is exposed with a high x-ray dose. For many medical questions, however, only an artifact-free reconstruction of the ROI is required. By the use of the diaphragm or diaphragm device according to the invention in the beam path of a CT apparatus, projection data can be generated that are sufficient for an artifact-free reconstruction of the ROI but expose the examination subject to a markedly reduced x-ray dose.

FIG. 10 shows the result of a reconstruction of projection data that have been generated by means of the use of a diaphragm device according to the invention. It is clearly recognizable that the ROI in the left image can be reconstructed without artifacts while the region outside of the ROI possesses artifacts. No difference in the reconstructed image of the ROI is thus shown at the respective right images of FIGS. 9 and 10.

Although modifications and changes may be suggested by those skilled in the art, it is the intention of the inventors to embody within the patent warranted hereon all changes and modifications as reasonably and properly come within the scope of their contribution to the art.

We claim as our invention:

1. A diaphragm for manipulation of x-ray radiation that emanates from an x-ray focus of a computed tomography apparatus and that irradiates an examination subject, the x-ray focus and the diaphragm being co-rotatable around a system axis to irradiate the examination subject, said diaphragm comprising:
    movable diaphragm elements that define a diaphragm aperture therebetween that, in turn, defines a spatial divergence of unattenuated x-rays passing through the aperture that strike a detector;
    said diaphragm elements being movable to dynamically adjust said diaphragm aperture; and
    said diaphragm elements being comprised of a material having a transmission factor for x-ray radiation that is different from zero to permit x-rays to propagate therethrough with a degree of attenuation that is less than 100%, to produce attenuated x-rays that produce evaluable measurement signals at said detector struck by the attenuated x-rays.

2. A diaphragm as claimed in claim 1 wherein said diaphragm elements are configured to give the x-ray radiation passing through the diaphragm aperture a fan-shape, defined by a fan angle and a cone angle, and wherein said diaphragm elements are movable to dynamically adjust said fan angle.

3. A diaphragm as claimed in claim 1 wherein said diaphragm elements are configured to give the x-ray radiation passing through the diaphragm aperture a fan-shape, defined by a fan angle and a cone angle, and wherein said diaphragm elements are movable to dynamically adjust said cone angle.

4. A diaphragm as claimed in claim 1 wherein said diaphragm elements are movable to adjust said diaphragm aperture dynamically depending on a current position of said x-ray focus around said system axis.

5. A diaphragm as claimed in claim 1 wherein said diaphragm elements are movable to cause only a region of interest of the examination subject to be irradiated with x-rays passing through the diaphragm aperture.

6. A diaphragm as claimed in claim 1 comprising a plurality of said movable diaphragm elements selected from the group consisting of two diaphragm elements and four diaphragm elements.

7. A diaphragm as claimed in claim 1 wherein each of said movable diaphragm elements has identical transmission properties for x-ray radiation.

8. A diaphragm as claimed in claim 7 wherein said transmission factor is in a range between 2 and 100.

9. A diaphragm as claimed in claim 8 wherein said transmission factor is in a range between 10 and 20.

10. A diaphragm as claimed in claim 1 wherein each of said diaphragm elements exhibits homogenous transmission properties for x-ray radiation.

11. A diaphragm as claimed in claim 1 wherein said diaphragm elements are configured to attenuate x-ray radiation striking the diaphragm elements with a constant attenuation factor in a direction of propagation of said x-ray radiation.

12. A diaphragm as claimed in claim 1 wherein said diaphragm elements are comprised of materials selected from the group consisting of titanium, copper, alloys of titanium, and alloys of copper.

13. A diaphragm as claimed in claim 1 wherein each of said diaphragm elements has a thickness in a range between 1 and 20 mm.

14. A diaphragm as claimed in claim 1 wherein each of said diaphragm elements has a constant thickness.

15. A diaphragm as claimed in claim 1 wherein each of said diaphragm elements has a diaphragm thickness that increases from a side of the diaphragm element facing the diaphragm aperture in a direction toward an exterior edge of the diaphragm element.

16. A diaphragm as claimed in claim 1 wherein each of said diaphragm elements has a diaphragm thickness that decreases from a side of the diaphragm element facing the diaphragm aperture in a direction toward an exterior edge of the diaphragm element.

17. A diaphragm device for manipulation of x-ray radiation that emanates from an x-ray focus of a computed tomography apparatus and that irradiates an examination subject, said x-ray focus and said diaphragm device being co-rotatable around a system axis to irradiate the examination subject, said diaphragm device comprising:
    a first diaphragm comprising first movable diaphragm plates that define a first aperture through which said x-ray radiation passes unattenuated to strike a detector, said first movable diaphragm plates having a transmission factor for x-ray radiation of zero; and
    a second diaphragm comprising second movable diaphragm plates that define a second aperture through which said x-ray radiation passes unattenuated to strike said detector, said second movable diaphragm plates having a transmission factor for x-ray radiation that is different from zero to permit x-rays to propagate therethrough with a degree of attenuation that is less than 100%, to produce attenuated x-rays that produce evaluable measurement signals at said detector struck by the attenuated x-rays.

18. A diaphragm device as claimed in claim 17 wherein said first movable diaphragm plates are adjustable with a high positioning precision and wherein said second movable diaphragm plates are adjustable with a high positioning speed.

19. A diaphragm device as claimed in claim 18 wherein said first diaphragm is located closer to said x-ray focus than said second diaphragm.

20. A diaphragm device as claimed in claim 17 wherein said first and second diaphragms are adjustable in parallel with each other.

21. A computed tomography apparatus comprising:

an x-ray source having an x-ray focus from which x-ray radiation emanates;

a diaphragm device mounted for co-rotation with said x-ray source around an examination subject to irradiate the examination subject with x-ray radiation from said x-ray focus; and said diaphragm device comprising a first diaphragm comprising first movable diaphragm plates that define a first aperture through which said x-ray radiation passes unattenuated to strike a detector, said first movable diaphragm plates having a transmission factor for x-ray radiation of zero, and a second diaphragm comprises of second movable diaphragm plates that define a second aperture through which said x-ray radiation passes unattenuated to strike said detector, said second movable diaphragm plates having a transmission factor for x-ray radiation that is different from zero to permit x-rays to propagate therethrough with a degree of attenuation that is less than 100%, to produce attenuated x-rays that produce evaluable measurement signals at said detector struck by the attenuated x-rays.

* * * * *